United States Patent [19]

Nicoli et al.

[11] E Patent Number: Re. 33,581

[45] Reissued Date of Patent: Apr. 30, 1991

[54] IMMUNOASSAY USING OPTICAL INTERFERENCE DETECTION

[76] Inventors: David F. Nicoli, 448 Mills Way, Goleta, Calif. 93117; Virgil B. Elings, 1155 Via Tranquilla, Santa Barbara, Calif. 93110

[21] Appl. No.: 72,699

[22] Filed: Jul. 13, 1987

Related U.S. Patent Documents

Reissue of:

[64] Patent No.: 4,647,544
Issued: Mar. 3, 1987
Appl. No.: 624,460
Filed: Jun. 25, 1984

[51] Int. Cl.[5] ..... C01N 33/53

[52] U.S. Cl. ..... 435/7.2; 250/461.1; 356/244; 356/317; 356/318; 356/354; 422/55; 422/82.05; 435/7.21; 435/970; 436/518; 436/519; 436/524; 436/527; 436/528; 436/531; 436/541; 436/805; 436/807; 436/909

[58] Field of Search ..... 435/7, 7.21, 970; 436/501, 518, 524, 528, 531, 541, 519, 527, 805, 807, 909; 356/317, 318, 337, 354, 244, 336, 338; 422/55, 62

[56] References Cited

U.S. PATENT DOCUMENTS 4,487,839 12/1984 Kamentsky ..... 436/518
4,521,522 6/1985 Lundström et al. ..... 436/531
4,537,861 8/1985 Elings et al. ..... 436/518

FOREIGN PATENT DOCUMENTS

83/01112 3/1983 World Int. Prop. O. .

*Primary Examiner*—Christine Nucker
*Attorney, Agent, or Firm*—William B. Walker; Laura Terlizzi

[57] ABSTRACT

Apparatus and method for providing an optical detection of a binding reaction between a ligand and an antiligand, including, a pattern formed by a spatial array of microscopic dimensions of antiligand material, ligand material interacting with the antiligand material to produce a binding reaction between the ligand and the antiligand in the pattern, a source of optical radiation including energy at at least one wavelength directed to the pattern at a particular incidence angle to produce scattering of the energy from the pattern in accordance with the binding reaction and with a strong scattering intensity at one or more Bragg scattering angles, and at least one optical detector located relative to the pattern and aligned with a Bragg scattering angle to detect the strong scattering intensity at the Bragg scattering angle to produce a signal representative of the binding reaction.

40 Claims, 3 Drawing Sheets

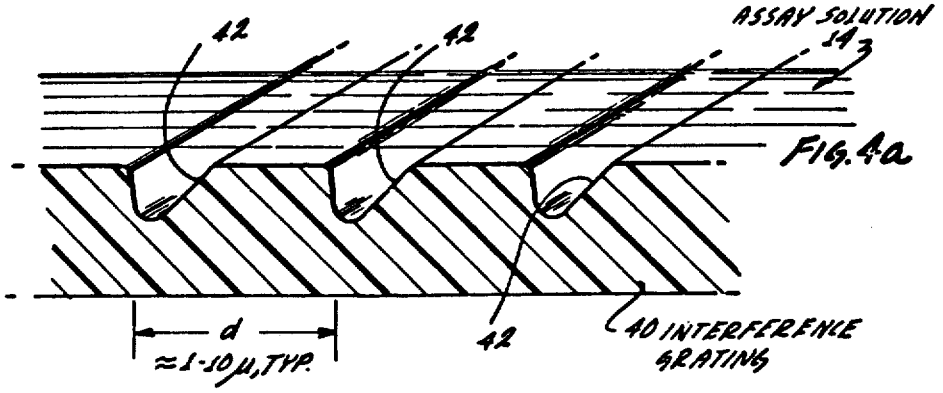
FIG. 4a
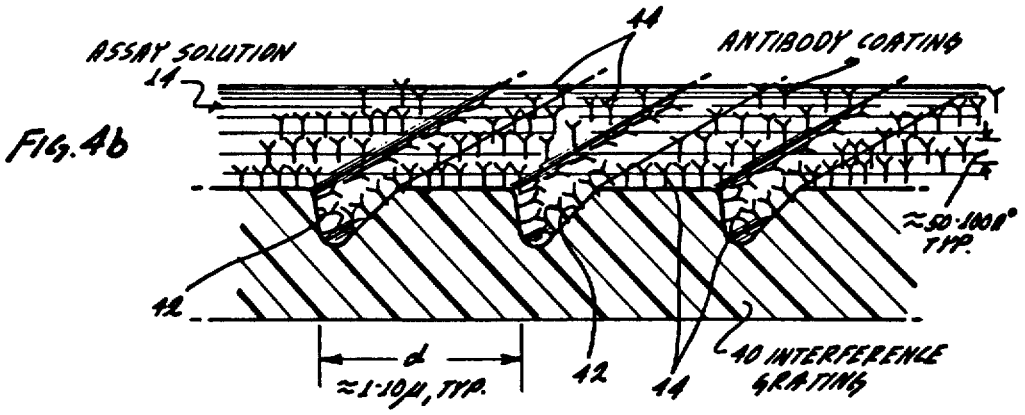
FIG. 4b
FIG. 4c
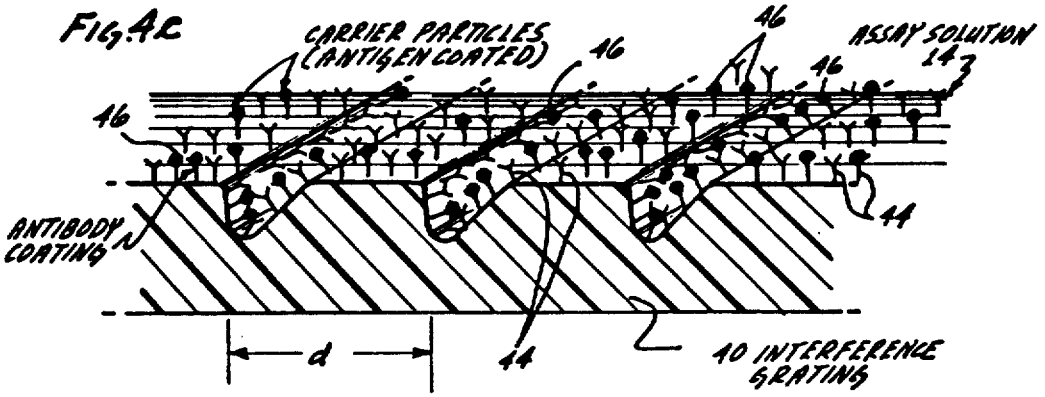

IMMUNOASSAY USING OPTICAL INTERFERENCE DETECTION

Matter enclosed in heavy brackets [ ] appears in the original patent but forms no part of this reissue specification; matter printed in italics indicates the additions made by reissue.

BACKGROUND OF THE INVENTION

1. Field of the invention

The present invention is directed to an immunoassay using optical interference detection. Specifically, the present invention provides for an immunoassay including a pattern to create a Bragg scattering peak which appears or changes when a particular chemical reaction occurs.

2. Description of the Prior Art

It is desirable in certain circumstances to measure very low concentrations of certain organic compounds. In medicine, for example, it is very useful to determine the concentration of a given kind of molecule, usually in solution, which either exists naturally in physiological fluids (e.g. blood or urine) or which has been introduced into the living system (e.g. drugs or contaminants). Because of the rapidly advancing state of understanding of the molecular basis of both the normal and diseased states of living systems, there is an increasing need for methods of detection which are quantitative, specific to the molecule of interest, highly sensitive and relatively simple to implement. Examples of molecules of interest in a medical and/or biological context include, but are not limited to, drugs, sex and adrenal hormones, biologically active peptides, circulating hormones and excreted antigens associated with tumors. In the case of drugs, for example, it is often the case that the safe and efficacious use of a particular drug requires that its concentration in the circulatory system be held to within relatively narrow bounds, referred to as the therapeutic range.

One broad approach used to detect the presence of a particular compound, referred to as the analyte, is the immunoassay, in which detection of a given molecular species, referred to generally as the ligand, is accomplished through the use of a second molecular species, often called the antiligand, or the receptor, which specifically binds to the first compound of interest. The presence of the ligand of interest is detected by measuring, or inferring, either directly or indirectly, the extent of binding of ligand to antiligand. The ligand may be either monoepitopic or polyepitopic and is generally defined to be any organic molecule for which there exists another molecule (i.e. the antiligand) which specifically binds to said ligand, owing to the recognition of some portion of said ligand. Examples of ligands include macromolecular antigens and haptens (e.g. drugs). The antiligand, or receptor, is usually an antibody, which either exists naturally or can be prepared artifically. The ligand and antiligand together form a homologous pair. Throughout the text the terms antigen and antibody, which represent typical examples, are used interchangeably with the terms ligand and antiligand, respectively, but such usage does not signify any loss of generality. In some cases, the antibody would be the ligand and the antigen the antiligand, if it was the presence of the antibody that was to be detected.

Implementation of a successful immunoassay requires a detectable signal which is related to the extent of antigen-antibody binding which occurs upon the reaction of the analyte with various assay reagents. Usually that signal is provided for by a label which is conjugated to either the ligand or the antiligand, depending on the mode of operation of the immunoassay. Any label which provides a stable, conveniently detectable signal is an acceptable candidate. Physical or chemical effects which produce detectable signals, and for which suitable labels exist, include radioactivity, fluorescence, chemiluminescence, phosphorescence and enzymatic activity, to name a few.

Broadly speaking, immunoassays fall into two general categories—heterogeneous and homogeneous. In heterogeneous assays, the purpose of the label is simply to establish the location of the molecule to which it is conjugated—i.e. to establish whether the labeled molecule is free in solution or is part of a bound complex. Heterogeneous assays generally function by explicitly separating bound antigen-antibody complexes from the remaining free antigen and/or antibody. A method which is frequently employed consists of attaching one of the members of the homologous pair to a solid surface by covalent binding, physical absorption, or some other means. When antigen-antibody binding occurs, the resulting bound complexes remain attached to this solid surface (compound of any suitably inert material such as plastic, paper glass, metal, polymer gel, etc.), allowing for separation of free antigen and/or antibody in the surrounding solution by a wash step. A variation on this method consists of using small (typically 0.05 to 20 microns) suspendable particles to provide the solid surface onto which either antigen or antibody is immobilized. Separation is effected by centrifugation of the solution of sample, reagents and suspendable beads at an appropriate speed, resulting in selective sedimentation of the support particles together with the bound complexes.

Notwithstanding the successful application of heterogeneous assay procedures, it is generally desirable to eliminate separation steps, since the latter are time-consuming, labor-intensive and sometimes the source of errors in the signal measurement. Furthermore, the more complicated protocols associated with heterogeneous assays make them less suitable for automated instrumentation of the kind needed for large-scale clinical applications. Consequently, homogeneous assays are more desirable. In the homogeneous format, the signal obtained from the labeled ligand or antiligand is modified, or modulated, in some systematic recognizable way when ligand-antiligand binding occurs. Consequently, separation of the labeled bound complexes from the free labeled molecules is no longer required.

There exist a number of ways in which immunoassays can be carried out. For clarity a heterogeneous format is assumed, although each approach can be utilized (with varying degrees of success) in a homogeneous format, given a suitable label which is modulated by the binding reaction.

In the competitive mode, the analyte, assumed to be antigen, is allowed to compete with a known concentration of labeled antigen (provided in reagent form in the assay kit) for binding to a limited number of antibody molecules which are attached to a solid matrix. Following an appropriate incubation period, the reacting solution is washed away, ideally leaving just labeled antigen-antibody complexes attached to the binding surface, thereby permitting the signal from the labels to be quantitated.

In another method, called the sandwich mode, the analyte, again assumed to be antigen, reacts with an excess of surface-immobilized antibody molecules. After a suitable incubation period, an excess of label-conjugated antibody is added to the system to react with another binding site on the antigen. After this reaction has gone to essential completion, a wash step removes unbound labeled antibody and other sources of contamination, permitting measurement of the signal produced by labels which are attached to antibody-antigen-antibody complexes. Any non-specific binding of the labeled antibody to the surface will, however, contribute to the signal.

In yet another approach, called the indirect mode, the analyte, this time assumed to consist of specific antibody, is allowed to bind to surface-immobilized antigen which is in excess. The binding surface is then washed and allowed to react with label-conjugated antibody. After a suitable incubation period the surface is washed again, removing free labeled antibody and permitting measurement of the signal due to labeled antibody. The resulting signal strength varies inversely with the concentration of the starting (unknown) antibody, since labeled antibody can bind only to those immobilized antigen molecules which have not already complexed to the analyte.

One of the most sensitive immunoassays developed thusfar is the radioimmunoassay (RIA), in which the label is a radionuclide, such as $I^{125}$, conjugated to either member of the homologous (binding) pair. This assay, which is necessarily heterogeneous, has achieved extremely high sensitivities, extending down to the vicinity of $10^{-17}$ molar for certain analytes. The obvious advantage of radioactive labeling, and the reason for the extremely high sensitivity of RIA-type assays, is that there exists negligible natural background radioactivity in the samples to be analyzed. Also, RIA is relatively insensitive to variations in the overall chemical composition of the unknown sample solution. However, the radioactive reagents are expensive, posses relatively short shelf lives and require the use of sophisticated, expensive instrumentation as well as elaborate safety measures for both their use and disposal. Hence, there is an increasing motivation to develop non-isotopic assays.

Fluorescence provides a potentially attractive alternative to radioactivity as a suitable label for immunoassays. For example, fluorescein (usually in the form of fluorescein isothiocyanate, or "FITC") and a variety of other fluorescent dye molecules can be attached to most ligands and receptors without significantly impairing their binding properties. Fluorescent molecules have the property that they absorb light over a certain range of wavelengths and (after a delay ranging from $10^{-9}$ to $10^{-4}$ seconds) emit light over a range of longer wavelengths. Hence, through the use of a suitable light source, detector and optics, including excitation and emission filters, the fluorescence intensity originating from labeled molecules can be determined.

Several heterogeneous fluorescence-based immunoassays (FIA) have been developed, including the FIAX/StiQ TM method (IDT Corp., Santa Clara, CA.) and the Fluoromatic TM method (Bio-Rad Corp. Richmond, CA.). In the former case, antigen is immobilized on an absorbant surface consisting of a cellulose-like polymer mounted on the end of a portable "dipstick", which is manually inserted into sample, reagent and wash solutions and ultimately into the florescence measuring instrument. A competitive reaction utilizing FITC-labeled monospecific antibody is typically employed. In the Bio-Rad assay kit, the solid surface is replaced by suspendable polyacrylamide gel microbeads which carry covalently-bound specific antibody. A sandwich mode is typically employed, with centrifugal sedimentation, followed by resuspension, of the beads for separation and measurement. Photon-counting techniques can be used to extend the sensitivity of the fluorescence intensity measurement.

Use of an enzyme as a label has produced a variety of useful enzyme immunoassays (EIA), the most popular of which is known as ELISA. In the typical heterogeneous format a sandwich-type reaction is employed, in which the ligand of interest, assumed here to be antigen, binds to surface-immobilized specific antibody and then to be enzyme-antibody conjugate. After suitable incubation, any remaining free enzyme conjugate is eliminated by a wash or centrifugation step. A suitable substrate for the enzyme is then brought into contact with the surface containing the bound complexes. The enzyme-substrate pair is chosen to provide a reaction product which yields a readily detectable signal, such as a color change or a fluorescence emission. The use of an enzyme as a label serves to effectively amplify the contribution of a single labeled bound complex to the measured signal, because many substrate molecules can be converted by a single enzyme molecule.

As discussed previously, it is generally desirable to eliminate the separation steps associated with typical heterogeneous assays and, instead, use homogeneous techniques. One of the first homogeneous assays to be developed was the fluorescence polarization immunoassay. Here, the polarization of the emission of the fluorescent dye label is modulated to an extent which depends on the rate of rotational diffusion, or tumbling, of the label in solution. Free labeled molecules which rotate rapidly relative to the lifetime of their excited states emit light of relatively random polarization (assuming a linearly polarized exciting beam, for example). However, when the label becomes attached to a relatively large bound complex, the rate of tumbling becomes relatively slow, resulting in fluorescence emission of substantially linear polarization (i.e. essentially unchanged). Unfortunately, this technique is limited in practice to the detection of low molecular weight ligands, e.g. drugs, whose rate of tumbling is sufficiently rapid to produce a measurable change in fluorescence polarization upon binding to the antiligand. The extent of modulation of the signal, in any case, is quite small.

Another useful florescence-based homogeneous techniques is the fluorescence excitation transfer immunoassay (FETI), also known simply as fluorescence quenching. Here, two different dye labels, termed the donor and the acceptor, or quencher, are used. The pair has the property that when the labels are brought close together, i.e. to within distances characteristic of the dimensions of antigen-antibody complexes, there is non-radiative energy transfer between the electronically excited donor molecule and the acceptor. That is, the acceptor quenches the fluorescence emission of the donor, resulting in a decreased intensity of the latter. In a typical competitive mode, the donor label is attached to the ligand of interest and the acceptor label fixed to the specific antibody. When ligand is present in the unknown sample, some fraction of the acceptor-labeled antibody binds to the free ligand, leaving a fraction of the labeled ligand unquenched and therefore able to emit fluorescence radiation. The intensity of the latter increases with increasing analyte concentration.

The principle drawback of the FETI technique is the requirement that the donor-labeled ligand be relatively pure. Substantial concentrations of labeled impurities produce a large background signal, making detection of a small change due to complexing all the more difficult. Along these lines, U.S. Pat. No. 4,261,968 describes an assay in which the quantum efficiency of a fluorescent label is decreased when the labeled antigen becomes bound to the antibody, resulting in a decrease in the total fluorescence emission of the sample solution.

One of the main factors which limits the sensitivity and reproducibility of all non-isotopic assays to varying degrees is the presence of background false signals. For example, in fluorescence-based assays the use of untreated blood serum may yield relatively high and variable background fluorescence levels due to the presence of proteins, bilirubin and drugs. In addition, there may exist variations in the absolute fluorescence intensity from one sample to the next due to fluorescence from sample cell surfaces, light scattering from impurities in solution, aberrations on optical surfaces, temperature dependent effects, etc. Problems related to impurities are particularly troublesome in homogeneous assays. However, the background false signal contributions are often relatively constant in time for any given sample measurement. Hence, a very useful technique for reducing the background contributions without the necessity of making additional control measurements is to determine the time rate of change of the signal. Such a rate determination in the early stages of the antigen-antibody binding reaction (i.e. when the rate is largest) should, in principle, be independent of the (constant) background level.

In principle, then, the rate determining procedure can be applied to any homogeneous assay technique, with the added advantage that the binding reaction need not be taken to essential completion, thereby resulting in a faster assay measurement. However, this approach becomes less feasible or advantageous the smaller the total signal change due to binding, relative to the background level. Hence, there are invariably practical limitations to the sensitivity which can be achieved using any of the existing homogeneous non-isotopic immunoassays, given the typical sources of background false signals, interferences and non-specific effects.

A previous invention by the same inventors as the instant application is embodied in patent application Ser. No. 463,658 filed Feb. 3, 1983 and entitled "Immunoassay". The previous invention is directed to a technique for detecting including scanning of a spatial pattern in order to detect a useful signal associated with the formation of antigen-antibody complexes. The prior invention therefore provides for not only producing a spatial pattern of a binding reaction but also for scanning this spatial pattern with input optical energy so as to detect an output signal having amplitude levels including a periodic component representing the labeled binding reaction.

SUMMARY OF THE INVENTION

The present invention is directed to a measurement technique for homogeneous immunoassays whereby the presence of analyte is detected quantitatively using optical interference and specifically a Bragg scattering peak. In order to simplify the description of the present invention it will be assumed that the analyte of interest or ligand consists of antigen molecules and the antiligand of interest is a specific antibody. In general, the concentration of the antigen in solution is determined indirectly by measuring the extent of binding of the antigen molecules to antibody molecules which are specific to the antigen of interest. As an example, the antigen and antibody may be members of a homologous binding pair.

In the present invention, the binding or complexing of the antigen to antibody is caused to occur preferentially at certain specified locations within the assay solution and typically on a two dimensional surface so as to form a spatial array of microscopic dimensions. The spatial array of antigen-antibody binding locations or sites is then illuminated from a particular direction by a beam of optical radiation. In the present invention it is preferable that the source of radiation be relatively coherent and monochromatic and therefore the preferred source of radiation is that produced by a laser. Alternatively, the particular embodiments of the invention may function using a source of illumination containing a broad range of wavelengths but with the detection at particular Bragg scattering angles.

The detection of any changes in the intensity of the scattered or transmitted or diffracted optical radiation due to changes in the extent of the antigen-antibody binding is provided by at least one optical detector. This optical detector is located at a specified Bragg angle and/or position with respect to the spatial array and the direction of incident illumination.

The present invention is distinct from the invention described in copending application Ser. No. 463,658 described above since the present invention relies on the physical principle of optical interference and is preferably implemented with the use of a coherent source of optical radiation. Typically, the coherent source of optical radiation has a wavelength either in the visible region or in the near UV or near infrared regions of the spectrum. In the present invention the spatial array is not scanned in order to detect the useful signal associated with the formation of antigen-antibody complexes. Rather, the existence of optical interference causes a useful signal to exist at particular spatial locations and/or directions with respect to the spatial array and the direction of incident illumination. The detection of a useful output signal is due to the antigen-antibody binding and requires no scanning of either the illuminating beam, the spatial array or the detector.

The present invention may be provided by an active antibody coating forming a regular periodic array of parallel stripes of microscopic dimensions on a solid flat surface. Both the width and center-to-center spacing for the stripes are of microscopic dimensions and are on the order of several wavelengths of the illuminating radiation. The array therefore forms an interference array to produce the optical interference so that a Bragg scattering peak may be detected. The array can also consist of a regular, periodic array of active antibody spots whose size and spacing are on the order of several wavelengths of light.

Other embodiments of the invention incorporate depositing an antibody coating on an already existing optical grating. Either the entire grating surface may be coated or just the peaks or valleys of the grating may be coated and with a detection of the Bragg scattered intensities provided in accordance with the incident illumination. The grating can function as either a transmission or a reflection grating.

BRIEF DESCRIPTION OF THE DRAWINGS

A clearer understanding of the invention will be had with reference to the following description and drawings wherein:

FIG. 4a illustrates an interference grating formed with a physically grooved surface;

FIG. 4b illustrates the grating of FIG. 4a with an antibody coating to form a second embodiment of the invention;

FIG. 4c illustrates the second embodiment of the invention and further including carrier particles to enhance the detection;

DESCRIPTION OF THE PREFERRED EMBODIMENTS

Figure 1:
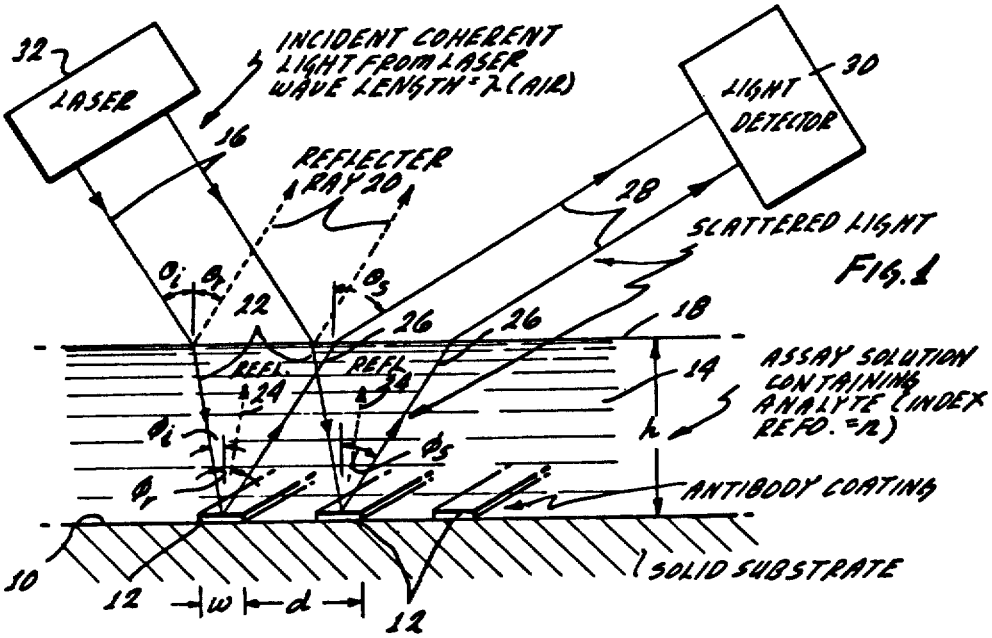
FIG. 1 illustrates a first embodiment of the invention incorporating a periodic spatial array of stripes of antibody on a solid substrate.

The first embodiment of the present invention is illustrated in FIG. 1 and includes a solid flat surface 10. The surface 10 is typically formed of glass, plastic, plastic coating on a solid surface, gel or some suitable inert material onto which specific antibody molecules are attached. This attachment is typically by means such as covalent binding or physical adsorption. The active antibody coating attached to the surface 10 is shown in FIG. 1 and has the form of a regular periodic array of parallel stripes 12. The antibody stripes 12 are in contact with an assay solution 14 which assay solution contains among other molecular components the antigen of interest.

The parallel stripes 12 of antibody each has a width w and with a center-to-center spacing d between each stripe in the array. Additionally the center-to-center spacing d is greater than the width w. Both w and d are of microscopic dimensions and as an example, the center-to-center spacing d is typically on the order of several wavelengths of the illuminating radiation. The very small size scale for the parallel array of stripes 12 is a specific requirement for the successful implementation of a detection device of the present invention using optical interference. Additionally the very small size scale is one of the important characteristics which distinguish the present invention from prior art devices.

A light beam is produced by a coherent source such as a laser 32 and with the light beam defined by incident light rays 16. The light from the laser 32 has a wavelength defined as $\lambda$(in air). The light rays 16 are directed toward the surface 10 which contains the array of closely spaced parallel stripes 12 of antibody. The assay solution 14 contains the analyte plus any additional needed assay reagents and with the solution in contact with the surface 10. For the specific example of the invention represented by the embodiment of FIG. 1, it is assumed that the portion of the assay solution 14 in contact with the surface 10 consists of a layer of liquid of uniform thickness h. This results in an air-liquid interface 18 having a flat surface which is parallel to the antibody bearing surface 10.

The light rays 16 of the illuminating light beam are directed to the air-liquid interface 18 at an angle of incidence designated by $\theta_i$ relative to a normal to the interface 18. The direction of the light rays 16 of the incoming light beam is aligned with respect to the antibody array 12 so that the plane of incidence containing the beam propagation vector is normal to the plane of the surface and perpendicular to the long axis of the individual antibody coated stripes 12. The incident beam of light energy is refracted at the air liquid interface 18. The resulting "internal" angle of incidence designated by $\phi_i$ in FIG. 1 is related to $\theta_i$ by Snell's Law as follows:

$$\frac{\sin \theta_i}{\sin \phi_i} = n \qquad (1)$$

where n is the index of refraction of the assay solution ($n_{air}=1$)

A fraction of the intensity of the incident light rays 16 is reflected at the air-liquid interface 18 due to the mismatch of the two indices of refraction. The reflected rays 20 are shown by dashed lines in FIG. 1 and leave the surface 18 at an angle $\theta_r$ equal to the angle of incidence $\theta_i$.

The refracted light beam formed by light rays 22 impinges on the solid surface 10 carrying the array of antibody stripes 12. In a similar fashion to the above, reflected rays 24 are produced if the index of refraction of the material comprising the solid surface differs from that of the assay solution 14. It is also possible to get multiple reflections within the layer of assay solution 14. If the substrate material is chosen to be index matched to the solution 14, there will be no reflected light rays. Normally, however, some light rays 24 of some intensity are reflected and with an internal angle of reflection $\phi_r$ equal to the incident angle $\phi_i$. The reflected beam defined by the light rays 24 after partial reflection at the air-liquid interface 18 emerges from the liquid at the angle $\theta_r$ equal to the original angle of incident $\theta_i$.

In addition to all of the various internal reflections and refractions, the incident radiation is scattered by the antibody coated array of stripes 12. In general, the polarizability of the antibody molecules differs from that of either the solid substrate 10 or the surrounding assay solution 14. Since the sources of the scattering which are the antibody coated stripes form a spatially periodic array, the antibody segments behave like a reflection grating.

A coherent source of radiation at a single wavelength or over an extremely narrow range of wavelengths is used to illuminate this "immunochemical grating". The physical phenomenon of optical interference results in a relatively strong scattering intensity at certain scattering angles $\theta_s$ and relatively low intensity at all other angles. The strength of the constructive interference at angle $\theta_s$ depends on the number of antibody stripes illuminated, the uniformity of their spacing distance d and their individual scattering efficiency. The efficiency depends on the extent to which the polarizability of the stripes differs from that of the surrounding liquid medium and of the solid substrate. The internal incident light rays 22 produce internal scattered light rays 26 having internal scattering angles $\phi_s$. External scattered light rays 28 are then produced having the external angles $\theta_s$ and with the internal and external scattering angles related by Snell's Law as follows:

$$\frac{\sin \theta_s}{\sin \phi_s} = n \tag{2}$$

The angles $\theta_s$ or their equivalent $\phi_s$ correspond to preferential scattering by the periodic array and specifically these scattering angles are [well known as the Bragg angles.] *referred to herein as the Bragg angles. The term "Bragg angles", as used herein, is defined as the angle between the normal to the solid substrate surface and the angle of the scattered, diffracted light waves, $\theta_s$.* The intensity of the preferentially Bragg scattered radiation, also of wavelength $\lambda$, is measured by a detector 30 shown in FIG. 1. The detector 30 may be of any suitable type such as a solid state photodiode or photomultiplier tube. The detector 30 is located at a distance from the scattering/reflecting surfaces, and as well as known in the art, suitable masks or apertures may be used to insure that the detector 30 receives only radiation which has been scattered at one of the preferential Bragg angles $\theta_s$.

The use of the immunochemical grating to perform the immunoassay operates as follows. Antigen molecules which are free in the assay solution 14 scatter light in all directions. This is true also for any other randomly positioned molecules in the solution as well as dirt particles or impurities contained in blood serum, etc. Therefore, the contribution to the light intensity detected by the detector 30 at the angle $\theta_s$, due to any of the sources of scattering in the solution 14, is relatively small because there will be no phase coherence between the scattered electric fields produced by these randomly positioned sources of light scattering. Such scattering will in general be distributed over all angles.

When a fraction of the antigen molecules becomes bound to the surface-immobilized antibodies forming the stripes 12, there is an increase in the scattered light intensity along the preferential angles $\theta_s$ due to an increase in mass of differing polarizability at the spatially periodic locations forming the array of stripes 12. In addition, the set of angles $\theta_s$ does not change with the addition of scattering mass at the periodic sites of the array since these angles are a function only of the parameters d, $\lambda$ and $\phi_i$ (or $\theta_i$) which parameters are predetermined. Therefore, the phenomenon of binding-enhanced Bragg scattering is ideally dependent only on the amount of scattering mass which becomes attached to the surface in a spatially periodic way which of course is the array of antibodies stripes 12. The binding of antigen can thereby be followed as a function of time by monitoring the increase in the scattered intensity at one or more of the preferential Bragg scattering angles $\theta_s$.

Figure 2A:
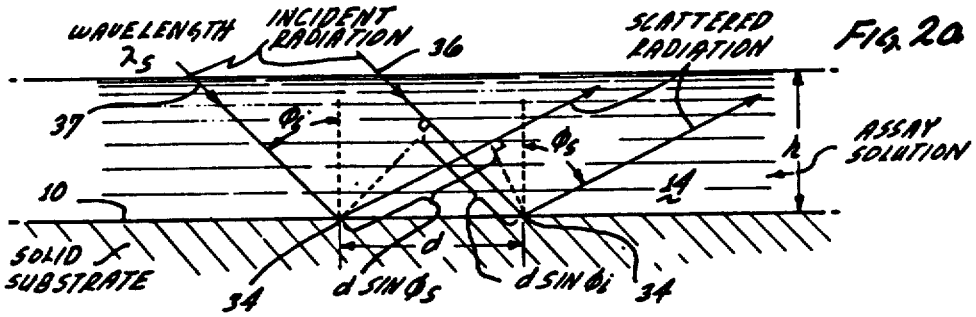
FIG. 2a illustrates an idealized periodic array of point-like scattering masses useful in explaining the operations of the present invention.

There is a specific relationship between $\theta_i$, d, $\theta_s$ and $\lambda$ required to produce a Bragg interference maximum in the scattered radiation from a periodic grating structure. As shown in the present invention, the assay solution 14 is in contact with the surface 10 and the antibody stripes 12 so that the specific relationship is expressed in terms of the internal angles $\phi_i$ and $\phi_s$ as shown in FIG. 2a. The internal angles define the angles of incidence and scattering within the liquid assay solution 14 which solution has an index of refraction n. In order to simplify the analysis the scattering array is considered to consist of a periodic array of point-like scattering masses 34 and with the distance between the points 34 or the periodicity to be d. A two dimensional array of stripes may be achieved simply by converting each point source 40 to a line source or a set of parallel line sources. The analysis provided by the simplified structure of FIG. 2a may be applied generally to all of the embodiments of the invention.

The incident wavelength of the illuminating radiation in the solution is defined by $\lambda_s$ and is related to the incident wavelength in air, $\lambda$, by the following:

$$\lambda_s = \frac{\lambda}{n} \tag{3}$$

The requirement for constructive interference at the angle $\phi_s$ is that the scattered electric fields produced by two adjacent scattering centers be in phase at a distant observer. The condition occurs when the difference in optical path lengths in solution, $\Delta L_s$, of two adjacent rays such as the two rays 36 and 37 shown in FIG. 2a is equal to an integral multiple of $\lambda_s$. This may be defined as, $$d|\sin \phi_i - \sin \phi_s| = m\lambda_s (m = 1, 2, 3 \ldots) \tag{4}$$

[→]

An equivalent expression is obtained which relates to the angles $\theta_i$ and $\theta_s$ and wavelength $\lambda$ in air and using Snell's Law as expressed in equations (1) and (2) as well as equations (3) becomes, $$d|\sin \theta_i - \sin \theta_s| = m\lambda (m = 1, 2, 3 \ldots) \tag{5}$$

[→]

As seen in FIG. 2a, the refraction of both the incident and scattered rays at the air-solution interface by the layer of assay solution 14 in contact with the antibody coated surface 10 does not change the Bragg equation defined above provided that the angles and wavelength of the radiation refer either to the fluid solution as defined by equation (4) or the air outside the solution layer as defined in equation (5).

A local maximum in intensity for the scattered optical radiation is obtained whenever the condition given by equation (4) or equation (5) holds. The scattering produced at the angle $\theta_s$ or $\phi_s$ corresponding to $m=1$ is referred to as the first order Bragg maximum; the scattering produced corresponding to $m=2$ is second order, etc. It is desirable to choose a incident angle $\theta_i$ and the order of interference m so that the angle $\theta_s$ differs significantly from the angle of reflection $\theta_r$. In this way, the change in scattering intensity at angle $\theta_s$ due to antigen-antibody binding is not obscured by the potentially large reflected intensity caused by a mismatch in indices of refraction at the air/solution and solution/surface interfaces. This is true even though ideally the reflected intensity is constant in time while the scattered intensity at angle $\theta_s$ increases with time as the extent of antigen-antibody binding increases.

Figure 2B:
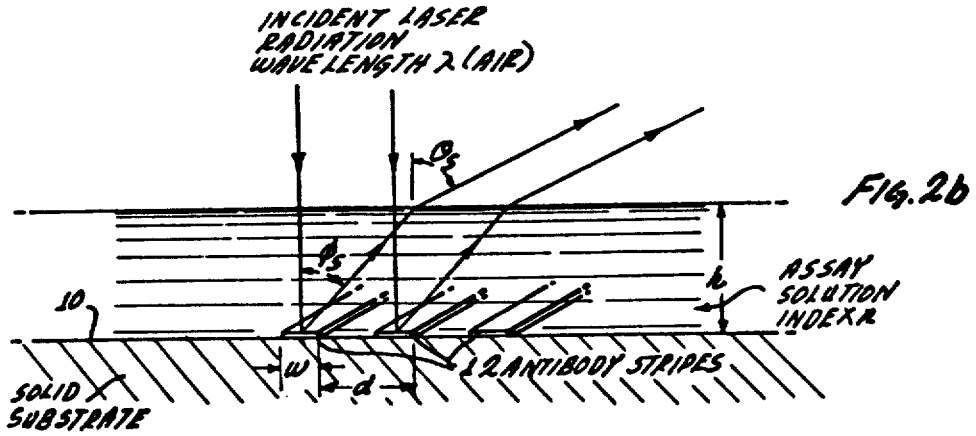
FIG. 2b illustrates the first embodiment of the invention with the incident radiation normal to the spatial array.

In order to simplify further the use of the immunochemical interference grating of the present invention, FIG. 2b illustrates a structure wherein the illuminating light beam produced by the laser 32 is incident along a normal to both the assay solution surface and the antibody coated surface. In such a structure, $\theta_i=\phi_i=0$ in both equations (4) and (5). The resulting Bragg interference condition which yields a maximum in the scattering at angle $\theta_s$ or $\phi_s$ reduces to:

$$d \sin \phi_s = m\lambda_s (m=1,2,3 \ldots) \quad (6)$$

or $$d \sin \theta_s = m\lambda (m=1,2,3 \ldots) \quad (7)$$

In the simplified structure of FIG. 2b the specularly reflected rays return along a normal directly back to the laser source 32 so that $\theta_r=\phi_r=0$.

A representative sample of first order (m=1) scattering angles $\theta_s$ corresponding to a range of antibody array spacing d for a plurality of choices of wavelength is shown in Table 1. The specific wavelengths chosen are $=\lambda 0.6328\mu$, $\lambda=1.15\mu$ and $\lambda=3.391\mu$. These particular wavelengths are available using a He-Ne laser but other wavelengths which lie either in the visible or near infrared regions of the spectrum are available from other sources including solid state lasers. The only requirement for the wavelength is that the solution be relatively transparent at that chosen wavelength.

As shown in Table 1, the longer the incident wavelength the larger the angle of the first order scattering maximum, $\theta_s$, for an array of given periodicity d.

TABLE 1

| d (microns) | $\theta_s$*($\lambda$ = 0.63$\mu$) | $\theta_s$*($\lambda$ = 1.15$\mu$) | $\theta_s$*($\lambda$ = 3.39$\mu$) |
|---|---|---|---|
| 1 | 39.3° | — | — |
| 2 | 18.4° | 35.1° | — |
| 3 | 12.2° | 22.5° | — |
| 4 | 9.1° | 16.7° | 57.9° |
| 5 | 7.3° | 13.3° | 42.7° |
| 10 | 3.6° | 6.6° | 19.8° |

*m = 1; 1st-order Bragg interference maxims.

Figure 2C:
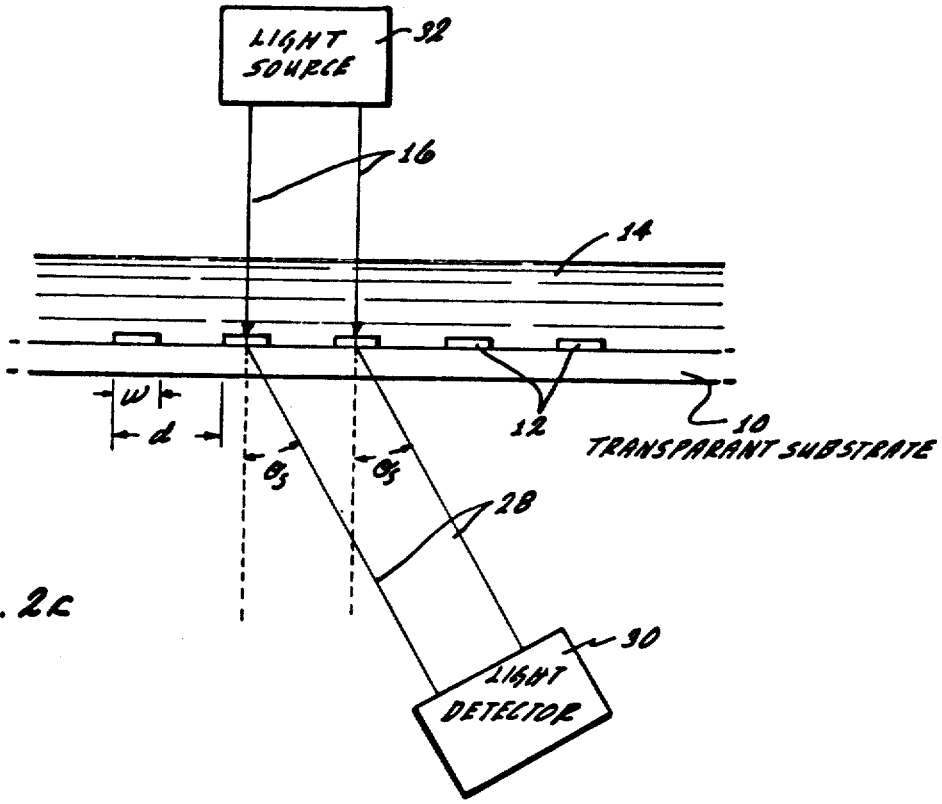
FIG. 2c illustrates the first embodiment of the invention with the detector placed so as to detect transmitted radiation (i.e. on the opposite side of the spatial array).

FIG. 2c shows a variation on the first embodiment of the invention in which the immunochemical grating acts as a transmission grating rather than a reflection grating, as previously described. In this version the detector 30 is located on the opposite side of the substrate as the illuminating light source 32. For simplicity, the incident light rays 16 are shown inpinging on the substrate 10 along a normal to the surface, analogous to FIG. 2b. In this case, the substrate 10 is chosen to be transparent, so that the Bragg scattered light rays 28 can pass through the substrate and be detected by the detector 30.

The Bragg scattering angles $\theta_s$ which correspond to constructive interference with local intensity maxima are again given by Equation (7) for the simplified case of normal incidence of coherent light of wavelength $\lambda$ and scattering order m. For the more general case of illumination at an angle of incidence $\theta_i$, the Bragg scattering angles $\theta_s$ are given by Equation (5). Considerations of experimental geometry (i.e. placement of light source, coated grating and detector), scattering efficiency and substrate transparency influences the choice of whether to use the immunochemical grating in the transmission or the reflection mode in carrying out an immunoassay measurement.

In order to provide for the structure of FIG. 1 and FIG. 2, the antibody must be successfully deposited on a solid substrate with a periodic array of very closely spaced stripes of uniform spacing and with the various dimensions typically being on the order of microns. There are a number of procedures by which the precision antibody coating may be accomplished, and some of these procedures will now be described.

In a first procedure, a continuous antibody coating is In a first procedure, a continuous antibody coating is initially provided to uniformly cover the entire substrate surface. The antibody molecules may be attached to the substrate surface either by physical adsorption or covalent binding. For example, when most plastic surfaces are immersed in a solution of protein molecules of a given kind, the surface acquires a monolayer coating of that molecular species. Once a coating is achieved, the next step consists of removing alternate stripe-like regions of the antibody coating of the desired width and periodicity. Equivalently, alternate stripe-like regions of the coating may be rendered chemically inactive with respect to their ability to bind the homologous antigen. The production of the strip-like regions may be accomplished by subjecting the antibody coated surface to a focused electron beam or ion beam which beam is scanned over the surface in a spatially periodic pattern to deactivate or denature antibody molecules in the desired stripe-like areas. To enhance the formation of the stripe-like regions a shadow mask, such as is fabricated by photolithographic techniques may be used in conjunction with or in place of the spatial scanning in order to render alternate stripes of antibody molecules inactive.

In place of the electron beam or ion beam a powerful focussed laser beam may be used to denature or otherwise render immunochemically inactive the antibody molecules in the spatial stripe-like regions. Additionally, an intense incoherent UV source, such as from a mercury lamp, together with a shadow mask placed near or in contact with the coated surface also may be used to accomplish the selective destruction of antibody molecules to form the stripe-like regions. In general, sources of ionizing radiation may be directed to the coated surface to produce the spatial pattern to form the immunochemical grating.

As an alternative to scanning the coated surface or using a shadow mask, an interference fringe pattern may be established over an extended region of the coated surface by intersecting two phase coherent laser beams. The interfering laser beams produce a fringe pattern which consists of uniformly spaced ribbons or bands of light which, if sufficiently intense and of a suitable wavelength may denature or destroy the antibody molecules in alternating stripe-like areas. Since certain types of molecules contain a number of ring-like resonant groups which absorb strongly in the UV region of the spectrum, it is desirable to use UV laser radiation to establish the fringe pattern.

Figure 3:
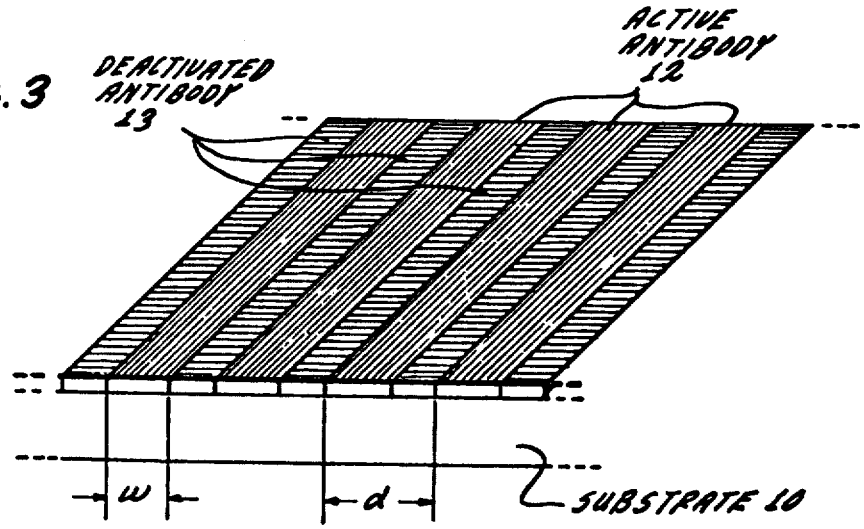
FIG. 3 illustrates a periodic immunochemical array consisting of alternating stripes of active and deactivated antiligand on a solid substrate.

FIG. 3 illustrates an immunochemical grating array consisting of alternating stripes of active and deactivated antibody. It is produced by first applying a uniform coating of active antibody on a flat substrate 10. Alternating stripe-like regions of deactivated antibody 13 are then produced using one of the procedures described above, leaving alternating stripes of active antibody 12 on the surface of the substrate. Such a grating array has the advantage that there exists minimal scattered intensity at the Bragg angles $\theta_s$ in the absence of antigen binding to the active portions of the antibody, due to the fact that the active and deactivated antibody regions ideally posses very similar polarizabilities (i.e. scattering efficiencies), causing the grating to effectively "disappear" when the antigen is not bound to the grating.

The immunochemical technique described herein posses two important characteristics which potentially give it a very high sensitivity and a great selectivity against interfering sources of false signal due to non-specific binding of molecules. In the first place the technique ideally involves a measurement "at null", in which the "baseline" signal is ideally zero in the absence of antigen-antibody binding. This results if the immunochemical grating consists of stripes of active antibody on the substrate surface which alternate with stripes of denatured, or otherwise inactive, antibody molecules. In this case light is scattered equally strongly from each kind of stripe before antigen (or labelled, mass-enhanced, antigen) binds preferentially to the active antibody stripes. Therefore, with respect to its scattering properties the coated substrate surface is effectively uniform, resulting in no Bragg interference peaks in the scattered light before the reaction occurs. The detected intensity at any of the Bragg angles $_s$ is therefore ideally very close to zero—i.e. is at null. This property causes the assay method to be very sensitive, because when a small amount of antigen binds to the stripes of active antibody, a scattering signal appears at the preferential Bragg angles $\theta_s$ where previously it was zero.

If the intensity to be detected at angle $\theta_s$ is extremely weak, due to a very small extent of binding of antigen (or labelled antigen, to enhance the scattering) to antibody, lock-in (i.e. phase-sensitive) detection techniques can be used to improve the signal/noise ratio of the measurement, as described previously. The important point is that detection of a small signal starting with nearly zero signal is inherently more sensitive and reliable, in practice, than detection of an equivalently small signal which is superimposed on a relatively large background signal, which in general will drift and otherwise vary in time, making it difficult to extract the desired signal.

A second important characteristic of this assay method is its relative insensitivity to non-specific binding of molecules at the antibody-coated substrate surface. Non-specific binding refers to the adsorption onto the coated substrate of molecules other than the antigen specific to the antibody on the substrate. This behavior may be a consequence of attraction of the molecules to the antibody molecules per se or to the underlying substrate (i.e. through electrostatic interactions). For the ideal immunochemical grating, consisting of alternating segments of active and deactivated antibody, non-specific binding of foreign molecules occurs with roughly equal probability for the active and inactive antibody. In this case, there is no contribution of such bound molecules to the intensity at any of the Bragg interference angles. That is, non-specific binding is not a source of false signal in any of the measured intensities providing the binding does not occur preferentially to either the active or inactive antibody coated stripes.

On the other hand, in the case in which the grating surface carries alternating stripes of active antibody and a substantially different material (e.g. polymer-coated antibody), both the detection-at-null property and the insensitivity to non-specific binding are compromised to some extent. In this case the immunochemical grating may give rise to a Bragg scattering pattern of intensity peaks at the angles $\theta_s$ in the absence of antigen-antibody binding due to the difference in scattering efficiencies of the two kinds of molecular species comprising the substrate coating. The closer the polarizabilities of the two kinds of coating stripes, the smaller will be the resulting quiescent Bragg intensities. However, in general the resulting assay is less sensitive than the one previously described, due to the fact that a small increase in intensity superimposed on a finite background signal must be detected. Also, in general non-specific binding of molecules leads to a false Bragg signal, because it is to be expected that the efficiency of non-specific binding differs for the two kinds of materials comprising the substrate coating.

The periodic antibody array may also be produced through the use of photopolymerization. Specifically, a thin layer of polymer solution is applied on top of the uniform antibody coating on the substrate surface. Using either a scanned focussed laser beam, a shadow mask or a stationary fringe pattern, all of which are described above, the polymer coating is exposed to sufficient radiation to polymerize alternate stripes of the polymer solution. The portions of the coating which remain unpolymerized are then washed away leaving a grating-like array of active antibody molecules, alternating with segments of polymer blocked antibody to which antigen cannot specifically bind.

A further method of fabricating the desired antibody array includes the use of photolithographic methods to lay down a periodic array of stripes of a particular substance which differs markedly from the substrate material in its ability to bind antibody. Specifically, a substance is chosen to which antibody readily attaches by physical absorption compared to the surrounding substrate surface so that the substrate surface will not attract antibody. Alternately, the deposited substance may be of a type to which antibody will not readily attach when compared to the surrounding substrate surface. As a specific example, macromolecules such as proteins generally do not absorb well onto glass surfaces. Photolithography is then used to construct a periodic array of thin polymer segments deposited on the glass. In this way the antibody is selectively absorbed onto the polymer coated surface but does not readily absorb onto the glass so that a periodic array of antibody absorbed onto the polymer segments is produced.

As described above, another important consideration for the interference immunoassay of the present invention is the inherent sensitivity of the immunoassay method. The binding of antigen molecules along to the antibody coated stripes in general yields a relatively small change in the overall scattered intensity at the Bragg angles $\theta_s$. The antibody which forms the grating array itself can be expected to produce Bragg scattered intensities at the same set of angles $\theta_s$. These intensities may be increased by the preferential deposition of additional scattering mass on the array by the binding of antigen to antibody. However, the total scattering in general is expected to be weak since there is only a relatively small mismatch between the indices of refraction or the polarizabilities of typical macromolecules and the surrounding solvent which is mostly water. As described below, the immunoassay may be enhanced by the use of a scattering label such as the use of carrier particles. Such means may therefore be used advantageously with the present invention.

It is desirable therefore to increase the scattering efficiency of the immunochemical grating by carrying out the assay using a form of labeled antigen where the label has the effect of greatly increasing the polarizability and therefore the scattering efficiency of the antigen. In one specific example, a competitive type assay may be performed in which free antigen, which comprises the unknown, and labeled antigen of known concentration, compete for binding to a limited number of antibody molecules which make up the grating array. Alternately, a sandwich type reaction may be used in the following manner. First, binding of the antigen to the antibody coated grating array is allowed to go to essential completion. Second, free labeled antibody is added in excess. The label consists of additional scattering mass. As the labeled antibody binds to the surface immobilized antigen, there is a monotonic increase in each of the Bragg scattering intensities at the various angles $\theta_s$.

As a specific example of a system which will increase the scattering efficiency, metallic ions are attached or otherwise complexed to the antigen for a competitive type assay or to the antibody for a sandwich assay so as in increase the scattering efficiency. A further increase in scattering power is achieved by making the label more massive than the antigen or antibody molecule itself. For example, more than one antigen or antibody molecule may be attached by adsorption or covalent binding to chemically inert carrier particles which scatter light particularly efficiently. A particularly good example of such an efficient carrier particle is a colloidal metal particle (sol) such as colloidal gold. It is known that most macromolecules absorb strongly onto such gold sols as well as other metal sols. The typical size range for such sols is 5 to 100 nm. The intensity of scattering produced by colloidal metal particles in solution exceeds by several orders of magnitude that which would be produced by antigen or antibody molecules along in solution.

Colloidal gold particles which have been coated with a variety of macromolecules (e.g. Avidin, various lectins, goat anti-rabbit IgG, etc.) are available commercially from a number of sources. In addition, carrier particles consisting of polystyrene latex or a similar material, which are preferably in the size range of 20 to 500 nm, may also be utilized to perform an assay using the immunochemical grating technique of the present invention.

As an alternative to the use of carrier particles which increase the scattering efficiency, other carrier particles may be used which absorb the incident light. In this way, as the absorbing particles become attached to the periodic array of antibody stripes, the incident light is scattered primarily from the uncoated areas of substrate between the stripes due to the index mismatch between the substrate and the assay solution. The absorbing carrier particles thereby decrease the scattering from the antibody segments. The preferential scattering from the uncoated segments of the surface produces the same net result which is an increase in the Bragg scattering intensities at the same set of angles $\theta_s$ or $\phi_s$ given by equations (4) and (5). The various parameters d, $\lambda$, n and $\theta_i$ are unaffected whether scattering occurs predominantly from the grating array represented by the antibody coated segments or from the complement to the grating array represented by the uncoated segments.

The above immunoassay technique may be used to detect the presence of antigen or antibody molecules which are located on the surface (i.e. in the membranes) of biological cells such as erythrocytes or lymphocytes. In this way cell typing may be performed to determine the concentration of cells which carry a particular type of antigen or antibody. In particular this immunoassay technique can be used to perform human red blood cell typing. If the cell-associated molecule is an antigen, the antibody-coated stripes discussed previously are used to construct the immunochemical grating. When the cell-associated molecule to be identified is an antibody, stripes composed of the homologous antigen molecules are used, alternating with stripe-like regions of inactive antigen.

In this variation of the assay, whole cells become attached to the grating surface in the immediate vicinity of the active stripes as a consequence of antigen-antibody binding. Consequently, the cell performs the physical function of the inert "carrier" particle described earlier, having the same effect of increasing the scattering due to a single binding event. Biological cells are considerably larger than inert carrier particles which are ideally chosen as scattering amplifiers which particles posses linear dimensions on the order of 1–10 microns. Hence for this application an immunochemical grating is designed with a relatively large stripe-to-stripe periodicity d, as shown in FIG. 1, which exceeds the largest cell dimension. In this way, when some cells become attached to the coated substrate the resulting pattern will resemble stripe-like regions of cells of periodicity d separated by gaps in which ideally no cells are attached. Because the cell dimensions may substantially exceed the wavelength of the exciting light beam, the efficiency of this assay in producing Bragg intensity peaks depends considerably on the cell size and shape as well as the grating parameters (i.e. dimensions w and d, FIG. 1).

Fluorescent labels or fluorescent carrier particles do not in general form any part of the present invention. Fluorescent sources behave as incoherent sources of radiation in which the emitted electric field from each fluorescent molecule does not bear a fixed phase relationship to the incident electric field. Therefore the field of fluorescent radiation does not display the sharp angular dependence exhibited by Bragg scattering regardless of the spatial locations of the emitting fluorescent labels. The existence of strongly fluorescent sources either in solution or on the substrate surface simply adds a background contribution to the intensity measured at any of the Brigg angles $\theta_s$. If this background were troublsome, it could easily be removed using an optical bandpass filter in front of the detector.

It has been previously shown with reference to Table 1 that it is preferable to use relatively long wavelength laser light, such as $\lambda \gtrsim 0.6\mu$, to illuminate the grating array. This allows for the choice of the largest periodicity d for the stripes. In addition, the use of relatively long wavelength light minimizes the fluorescent background intensity from most serum samples since naturally fluorescing sources are generally excited at shorter wavelengths.

The embodiment of the present invention, disclosed in FIG. 1, requires a periodic array of microscopically spaced stripes of antibody formed on a flat substrate surface. Another embodiment of the invention is disclosed with reference to FIGS. 4a through 4c.

In general, this other embodiment of the invention is an actual interference grating having a physically grooved surface to form the solid substrate on which antibody is immobilized and to which antigen-antibody binding occurs. The grating consists of a solid or semi-solid material 40 and is preferably a transparent material, such as plastic, and with one surface containing a periodic structure of closely spaced grooves 42 of spacing d as shown in FIG. 4a. The surface of the substrate 40 which contains the spatially periodic grooves 42 will scatter light preferentially along the Bragg angles defined by equation (5). Again, the grating can be used in either the backscatter (i.e. reflection) mode or the transmission mode.

The individual scattering sources at each point along the grooved structure do not scatter light with equal efficiencies due to the detailed shape and structure of the groove pattern. Therefore, the scattering along the angles $\theta_s$ given by equation (5) is enhanced due to constructive interference. The efficiency with which the grating of FIG. 4a will Bragg scatter coherent light into the various orders on m values is a function of the angle of incidence, the wavelength and the polarization of the incident radiation, the index of refraction of the grating material 40, the groove density and uniformity and the detailed shape and orientation of the grooves 42.

The major advantage in the use of a structure such as shown in FIG. 4a to form the solid substrate is that the entire grating surface may be coated with antibody 44 to produce a second embodiment of the invention shown in FIG. 4b. This avoids entirely the task of depositing on a flat surface a periodic array of very closely spaced stripes of antibody as shown in FIG. 1 or alternating active/deactivated stripes as shown in FIG. 3. The coating process is accomplished by immersing the solid grating material 40 into a solution of antibody in an appropriate buffer, for a period of time. A monolayer of the antibody molecules 44 forms on the grooved plastic surface by physical adsorption.

The thickness of the macromolecular monolayer 44 is typically only 25 to 100 angstroms compared to the characteristic groove dimensions of fractions of a micron, or larger. Therefore, the surface of the coated grating, as shown in FIG. 4b, mimicks even to fine detail the features of the original grating surface as shown in FIG. 4a. As an alternate to the use of physical adsorption, the plastic surface of the substrate 40 may contain chemically reactive groups and the antibody molecules 44 may be attached to the plastic coating by covalent binding using standard chemical procedures.

The plastic grating 40 may be obtained commercially. As an example, acceptable precision gratings can be obtained from commercial companies such as Edmund Scientific Company of Barrington, N.J. One particular grating which may be used is found in a recent catalog from Edmund Scientific and bearing catalog number 40,267. This particular grating is formed of a flexible sheet of acetate and with one surface containing a periodic structure of closely spaced grooves. This particular grating includes 13,400 grooves/inch which results in $d=1.90\mu$. The thin plastic sheet forming the substrate is essentially transparent and can thereby function as either a transmission of reflection grating.

Coherent light is directed to the grating 40 and as a specific example coherent light may be directed along a normal to the surface of the grating 40. This is as shown in FIG. 2b which produces a set of Bragg scattered rays along the angles $\theta_s$ as given by equation (7). When the structure of FIG. 3b is used in the reflection mode, the scattered beams are located at angles $\theta_s$ less than 90° as defined in the above equation and as exemplified in Table 1. When the structure of FIG. 3b is used in the transmission mode, the scattering is in the forward direction with $\theta_s$ greater than 90°. This is because the original values of $\theta_s$ given in equation (7) are replaced by $180°-\theta_s$.

When the particular grating, catalog number 40,278 from Edmund Scientific is used, the scattering is relatively strong in the first order $m=1$ and much weaker for the second and higher order scattering peaks. Using the red light from a HeNe laser, $\lambda=6328$ angstroms, and with the incident light normal to the surface, a strong first order Bragg spot of light is achieved in air at $\theta_s \approx 19.5°$.

The interference grating 40 as uniformly coated with antibody 44, is therefore used to detect quantitatively the amount of antigen which becomes bound to the corrogated or grooved surface. Before the antigen becomes bound, a set of Bragg scattered intensities may be measured with the angles $\theta_s$ given by equation (5) since the physical periodic grating is in contact with the assay solution 14. Because the measurement of interest is the increase in one or more of the Bragg scattered intensities due to the addition of antigen to the grating surface, the amount of scattering which occurs initially or before antigen binding has occurred should be minimized.

To achieve this minimum, the index of refraction of the plastic, or other material forming the interference grating, is closely matched to the index of refraction of the assay solution. If this is accomplished then there will be relatively little initial Bragg scattering. This is because the assay solution fills in the grooved structure 42 of the grating. This approximately index matches the grooves 42 to the assay solution so that the grating tends to disappear. The actual levels of the resulting scattered intensities at the angles $\theta_s$ depend on the closeness of the match of the indices of refraction of the solution and the grating material as well as the polarizability of the antibody coating. In addition, the coating itself may serve to some extent as an index-matching layer.

It also may be desirable to add additional chemical compounds, such as sucrose, ethylene glycol etc, to the assay solution to aid in the index-matching. These compounds can be added if they do not adversely affect the antigen-antibody binding reaction. The addition of these compounds will increase the index of refraction of the solution thereby promoting a closer match to that of the antibody-coated grating material. This is because the solution is primarily water and has an index of refraction of approximately 1.33. The typical plastics would have a higher index of refraction since most plastics have indices of refraction in the range 1.40 to 1.50.

As an alternative to trying to increase the index of refraction of the solution, the grating may be fabricated using a plastic polymer material which has an index of refraction more closely matched to that of the assay solution. In particular the polymers (e.g. polymethyl methyacrylates) that are used to construct soft contact lenses have indices of refraction more closely matched to water. Additionally, polyacrylamide gel may be used to construct a grating since typically 90 to 95% of the gel consists of trapped water. The starting solution for the gel, before the gel is cross linked, is poured onto a master grating. The master is made of a hard material such as metal or glass so that the master grating acts as a mold. After polymerization, the slab of gel is lifted away from the master grating to yield an accurate impression of the grating. Antibody molecules may then be covalently bonded to the corrogated surface of the gel.

Once the basic structure such as shown in FIG. 3b is produced, then the scattered intensities, which are measured at one or more of the Bragg angles $\theta_s$, increase with increased binding of antigen to the antibody coated surface. This is accomplished since the addition of antigen at each point on the surface in general results in increased scattering due to a further mismatch in the polarizabilities of the grating surface with the antibody coating and the surrounding solution. Essentially, the addition of the antigen provides for a poor index matching of the grating to the solution which results in an increase in scattering. As an alternative to the above, the addition of the antigen may provide a decrease in the Bragg scattering intensities if the antigen provides for a better index matching of the grating to the solution. This would also be an acceptable type of measurement since the change of intensities for the Bragg scattering, whether positive or negative, may form a reliable indication of the antigen-antibody binding.

Since the change in the Bragg scattered intensities, due to the binding of antigen alone to the antibody coated grating surface, is fairly small, this change can be intensified through the use of a labeled antigen or antibody as described above. The label consists of additional polarizable material which greatly increases the scattering due to the binding of a single antigen molecule to the grating surface. One particular structure, as described above, is the use of tiny carrier particles such as collodial gold particles preferably of a dimension from 5 to 20 mn to which are absorbed or otherwise attached the antigen or antibody molecules.

Specifically, antigen coated collodial gold particles of a known concentration may be used in a competitive mode assay as the tiny gold particles leave the surrounding assay solution and become attached to the grating surface. The grating surface thereby produces a dramatic increase of its Bragg scattering efficiency. This occurs when the carrier particles are much smaller than the characteristic dimensions of the grooves, which make up the grating surface, so that the deposition of these particles on the surface resembles a fine metallic coating as shown by the particles 46 in FIG. 3c. It is well known that an interference grating which has been coated with a thin metallic coating, such as by vacuum deposition, produces far stronger Bragg scattering than does a grating of transparent plastic. Therefore if the antibody coated grating is initially well indexed matched to the assay solution, the increase in Bragg scattered intensity at a given angle $\theta_s$, due to random deposition of individual metal particles on the surface, is very pronounced. Non metallic carrier particles such as polystyrene beads may also be used to enchance the scattering efficiency of the grating.

The apparatus of the present invention may also have the sensitivity of the assay enhanced by using particular detection techniques. For example, in some applications it may be necessary to detect the Bragg scattered light at very low intensity levels. In order to provide for the detection, the technique of lock-in or phase-sensitive detection may be employed. This technique can be utilized in two ways. In the first place, if the Bragg scattered light intensity is weak relative to a background light level unrelated to the laser source, the incident laser radiation may be periodically chopped or otherwise modulated and a lock-in amplifier used on the detector at angle $\theta_s$ to separate the desired intensity signal at angle $\theta_s$ from the ambient light level. In the second place, the phase-sensitive technique may be used to advantage when the Bragg scattered intensity at angle $\theta_s$ is very weak relative to the surrounding scattered light intensity (i.e. at adjacent angles) which occurs over a broad range of angles. Such as relatively high level of scattered intensity may be caused by grating imperfections and background or from scattering from molecules, dirt, etc. in the sample solution (which scattering may or may not be isotropic). In this case it may be desirable to achieve a periodic scan in detection angle $\theta_s$ within a small range of angles encompassing the desired angle $\theta_s$ and use phase-sensitive detection to extract the desired intensity signal due to Bragg scattering. This may be achieved by translating the detector in periodic fashion so as to sample a range of angles $\theta$. Alternatively, the detector may be kept stationary and the grating substrate/solution layer rocked, or rotated, back and forth slightly to cause the desire Bragg scattering spot to sweep back and forth past the detector.

It should also be noted that a multi-element detector array may be used to advantage in conjunction with this invention. Using such an array one may simultaneously detect scattered light over a wide range of angles $\theta$ which encompass more than one of the Bragg angles $\theta_s$. Measurement of the scattered intensity at several of the angles $\theta_s$, i.e. as a function of the interference order m, provides an internal cross-check on the Bragg result and may be used to discriminate against background false intensity signals and ultimately to improve the signal/noise ratio and overall reliability of the measurement. Also, use of a high resolution multi-element detector array has the additional advantage that precise alignment of the detector with respect to the grating orientation is no longer required. With many detectors covering a range of angles $\theta$, by definition there is no longer the possibility of misalignment of the detector with resulting loss of the desired signal at angle $\theta_s$.

As discussed above, a limitation on the sensitivity of this immunoassay method is imposed by the existence of background light at the preferential Bragg angle $\theta_s$ due to nonidealities in the immunochemical grating as well as scattering by molecules and particulates in the sample solution. An additional method of enhancing the signal/noise ratio of the measurement is to determine the initial rate of the binding reaction. This is, the time rate of change of the detected intensity at angle $\theta_s$ is determined early in the course of the binding reaction. Ideally, this should result in a measured quantity which is relatively insensitive to the background intensity, which is presumed to be approximately constant over the time course of the rate determination. This procedure possesses the additional advantage that it produces a value relatively quickly—i.e. it is not necessary to wait for the binding reaction to go to essential completion. Such a measurement of the initial rate, or velocity, of binding to the grating surface ideally discriminates against all sources of background light, both associated with grating imperfections and solution scattering as well as ambient light levels unrelated to the laser radiation.

One of the advantages of our invention is that the useful signal is produced by light scattering from the entire illuminated region, thus causing an interference peak due to the periodicity of preferential scattering sites which exist over that region. Therefore, small random defects in the pattern of scattering sites do not contribute significantly to the signal. This is quite different from our previous invention, copending application Ser. No. 463,658, which utilizes the principle of synchronous detection of a spatial pattern, in which small defects in the pattern—e.g. bright fluorescent impurity spots on the pattern—would contribute to the apparent fluorescent signal. In the present invention, random, isolated defects such as dirt specks or scratches on the pattern surface result in scattering in all directions, but will not in general cause the scattering to be concentrated along any of the preferential Bragg angles. The resulting background intensity which occurs at any Bragg angle will be small compared to the scattered intensity caused by the periodic array.

This result carries an important implication for the requirements of the production of these periodic arrays of antibody stripes. That is, the individual stripes which comprise the periodic array do not need to be manufactured to precise dimensional tolerances. For example, discontinuities in individual stripes or blurred, nonuniform edges have little effect on the quality of the Bragg scattering signal (i.e. on the intensity of the Bragg spot). What does matter, of course, is that the stripe-to-stripe spacing (i.e. the periodicity) be maintained over the long range of the illuminated region of the surface Hence, for example the dimensional tolerances required for the antibody stripe pattern are not nearly as stringent as those required for typical electronic integrated circuits.

We have disclosed the possibility of using two different kinds of periodic arrays for an immunoassay. One array consisted of alternating stripes of specific, active antibody molecules and denatured antibody molecules (in which the molecules are made inactive by an intense beam of ultraviolet light or ionizing particles, such as electrons) on a flat surface. The other consisted of specific antibody attached (e.g. by adsorption) uniformly to the surface of an actual physical grating. It is important to point out that these two kinds of grating surfaces act differently with respect to the problem of nonspecific binding of tagged molecules to the surface. In both cases it is assumed that the tagged molecules bind to the surface at random locations. On the flat surface, in which the "grating" exists only by virtue of the pattern of active antibody stripes, these particles yield random scattering in all directions and, therefore, do not contribute significantly to the intensity of the Bragg peak.

On the physical grating surface, on the other hand, those particles which bind nonspecifically give the same signal as those which bind specifically to antibody. That is, the physical grating surface does not discriminate against nonspecific binding. Hence, in any assay in which the ultimate sensitivity is limited by non-specific binding of tagged molecules to the surface, the flat surface with alternating stripes of active antibody would be the preferable embodiment.

As described previously, this invention utilizes the physical principle of optical interference to detect antigen-antibody binding on a surface. In the description thusfar, a particular kind of scattering pattern was utilized, a periodic array which resembles a diffraction grating. The grating consists of either a parallel set of stripes of active antibody molecules attached to a flat surface or an actual physical grating (i.e. periodically ridged surface) which is everywhere coated with active antibody. In both cases one obtains an interference grating which produces relatively strong scattering intensities along certain preferential directions, corresponding to the Bragg scattering angles. The intensity of each of the Bragg peaks, or "spots", increases with increasing efficiency of scattering due to additional binding of tagged molecules to the surface-immobilized antibody.

However, it is important to appreciate that Bragg scattering from a uniform, grating-like array of parallel, periodic scattering sites represents only one approach by which optical interference can be utilized to detect antigen-antibody binding at a surface. A more general approach consists of using some arbitrary, fixed pattern of active antibody sites on a surface. One then illuminates this pattern with coherent light from a laser source at a given angle of incidence in either the transmission or reflection mode. One can then use a lens located some distance from the pattern surface to produce an image a further distance away, on the so-called "transform" plane. The resulting image on the transform plane, consisting of some two-dimensional pattern of intensities (i.e. regions of high intensity and low intensity) is, in fact, the spatial Fourier transform of the original antibody-coated pattern of scattering sites (i.e. on the "object" plane). In the previous case, in which the starting antibody pattern consisted of a simple array of parallel stripes of uniform spacing, the resulting spatial Fourier transform is a set of discrete "spots" of light, lying along a straight line in the transform plane, which are the Bragg peaks corresponding to a given array periodicity. In the more general case of an arbitrary starting pattern of antibody coating, the resulting spatial Fourier transform intensity pattern will be more complicated (and unique to a given starting pattern of scattering sites on the object plane).

As an example, the pattern might consist of two sets of parallel, periodic stripes with one set of stripes intersecting normally to the other set, thereby creating a rectilinear array resembling a woven fabric. In effect, the pattern consists of two perpendicularly-crossed gratings. The resulting intensity pattern on the transform plane consist of two sets of Bragg scattering spots. Each set of spots lies along a line which is perpendicular to the long direction of the set of stripes from which it derives. The two linear arrays of spots are therefore mutually perpendicular, forming a cross-like pattern of spots, in which the spot intensity decreases with increasing distance from the center of the array (i.e. with increasing order of Bragg interference). The spacing of the spots which form each linear segment of the array is determined by the periodicity of the corresponding set of stripes and is given by the Bragg scattering relation (discussed previously) and the location of the transform plane.

The point to recognize is that this more complicated pattern of scattered intensities can as well be detected by using more than one detector, located at several points on the transform plane where intensity maxima are expected to occur, or by using a mask which is designed to "recognize" the expected Fourier transform pattern and to pass some portion of the intensity distribution to a single detector. Hence, by using some combination of masks and/or detectors, one can detect changes in the scattered intensity pattern which occur as a result of changes in the degree of binding of tagged molecules to an arbitrary pattern of antibody molecules attached to a surface. The simple array of periodic, parallel stripes is our preferred embodiment because of its simplicity.

The embodiments of the present invention have been described with the use of a coherent source of illuminating radiation such as a laser. However, it should be appreciated that a source of light having a relatively broad range of wavelengths may also be used. This is because the grating, having a given periodicity d, uniquely disperses the incident radiation into the scattered rays of different angles, $\theta$hd s, corresponding to the differing wavelengths from the source of light and with each different angle, $\theta_s$, in accordance with the equations (4) and (5). Therefore, one or more detectors located at different angles $\theta_s$ (or a multi-element detector array) to used to collect information over the entire dispersed spectrum over a relatively large range of angles. As the grating scatters more efficiently with an increase in antigen-antibody binding at the surface, the intensities over the entire spectrum increase. It is to be appreciated however, that it is simpler to provide for the detection using a laser source because in that case all of the Bragg scattering is concentrated into a small number of spots or angular positions.

For all of the embodiments of the immunoassay technique described herein, the intensity of a Bragg scattering maximum (i.e. peak) located at a particular preferential Bragg angle $\theta_s$ will in general increase with increased extent of antigen-antibody binding at the grating surface. That is, the greater the amount of mass bound to the substrate surface, the greater the Bragg scattered intensity. However, this relationship between the Bragg scattering intensity and the amount of antigen (or antibody) bound to the immunochemical grating will in general not be linear, because the scattering involves coherent radiation. Therefore the immunoassay instrument which is designed in accordance with the method described herein must ultimately be calibrated using standard samples of antigen (or antibody) of known concentration. The need to construct such standard calibration curves is a requirement common to all existing immunoassay methods.

It should be appreciated that only a relatively small sample solution volume is needed for the normal functioning of this immunoassay technique. The thickness of the layer of solution in contact with the grating surface should ideally be kept as thin as possible, in order to limit the time needed for the molecules comprising the analyte, plus possibly other reagents, to diffuse to the vicinity of the grating surface, thereby permitting binding. Also, the dimensions of the grating can be kept relatively small (e.g. on the order of 1-10 mm), since only that portion of the grating which is illuminated by the incident laser radiation can contribute to the desired Bragg intensity signal. This feature of small sample volume is generally useful, and is consistent with the requirement that the method posses a high sensitivity. The fact that the layer of solution can be quite thin means that samples which are nominally quite turbid may be employed, permitting the incident laser light and resulting Bragg scattered light to traverse the liquid layer with relatively little attenuation.

It is useful to point out that the technology described herein permits the design of an apparatus which allows more than one immunoassay to be performed simultaneously on a single small volume of sample solution. Several immunochemical gratings of different periodicities, each prepared in accordance with previous suggestions and containing stripes of a different specific antibody (let us say), can be located in close proximity on a single substrate surface, with the entire set of arrays in contact with the sample solution and all gratings illuminated with the same laser beam (perhaps expanded in size using suitable optics). In this case several sets of Bragg "spots" of relatively high intensity can be detected by a set of detectors (or a multi-element detector array, as described previously) suitably located at the angles $\theta_{s1}$, $\theta_{s2}$, $\theta_{s3}$, etc. In this way one can, in principle simultaneously follow the time course of binding, and thereby determine the concentration of, more than one type of molecule contained in the sample solution.

It can be seen therefore that the present invention is directed to an apparatus and method for providing an immunoassay using optical interference, and specifically by measuring the binding of the antigen molecules to antibody molecules at preferential specified locations on an assay surface, and with these preferential specified locations forming a spatial array which when illuminated by incident radiation provide for scattering of the incident radiation along a particular angular direction characterized as Bragg scattering. The intensity of the Bragg scattered radiation is then detected and with the level of the detected Bragg scattered radiation detected either at a particular point in time or with changes in the intensity of the detected Bragg scattered radiation detected over a period of time so as to provide for a measure of the immunoassay. The spatial array of antigen-antibody binding locations forms an immunochemical grating and with such grating having a number of different embodiments as disclosed in the present invention.

It is useful to summarize those essential features, discussed earlier, which define this invention. One utilizes a chemically active, predetermined pattern which is attached to a surface. This pattern consists of predetermined regions, or areas, of active ligand or antiligand molecules (e.g. antigen or antibody) surrounded by regions, or areas, which contain no such material, or ligand or antiligand which has been rendered chemically inactive (i.e. with respect to its ability to bind the complement molecule). The physical basis for the invention is the phenomenon of optical interference. Optical radiation, preferably of nearly a single wavelength, is directed onto the immuno-chemical pattern-bearing surface. The light is scattered in general from all points on the surface, with the efficiency of scattering varying from one point to the next due to the spatial modulation of the optical properties of the surface (e.g. absorbance, scattering, transmission, etc.) caused by ligand-antiligand binding reactions which occur on the pattern surface. These reactions may occur in conjunction with reactions which also occur in the surrounding solution containing the analyte. The individual scattered light waves undergo optical interference at all points in the surrounding space, resulting in general in an enhancement of the scattered light intensity at one or more locations and/or angles in space, provided that a particularly effective pattern design is chosen. The pattern need not be periodic; the preferred embodiment of a Bragg interference grating discussed at length herein, was chosen for convenience. One or more optical detectors can then be used at one or more of these points or angles to detect the enhanced intensity(ies), and thereby deduce the extent of ligand-antiligand binding which has occurred.

Although the application has been described with reference to particular embodiments, it is to be appreciated that various adaptations and modifications may be made and the invention is only to be limited by the appended claims.

We claim:

[1. An apparatus for providing an optical detection of a binding reaction between a ligand and an antiligand, including, a predetermined pattern formed by a spatial array having a plurality of elements of microscopic dimensions of antiligand material, ligand material interacting with the spatial array of antiligand material to produce a binding reaction between the ligand and the antiligand in the pattern, a source of optical radiation directed toward the pattern to illuminate the plurality of elements of the spatial array to produce an optical interference pattern in accordance with the modulation of the optical properties of the predetermined antiligand pattern due to the binding reaction, and one or more optical detectors to detect the strong scattering intensity at one or more angles to produce a signal representative of the binding reaction.]

[2. The apparatus of claim 1 wherein the predetermined pattern is formed by a plurality of stripes of antiligand material, each stripe having a width of microscopic dimensions and separated from each other by a constant microscopic dimension.]

[3. The apparatus of claim 2 wherein the plurality of stripes of antiligand material is formed by antiligand material supported on a flat continuous surface.]

[4. The apparatus of claim 1 wherein the spacial array if formed by antiligand material supported on a grooved surface forming an interference grating.]

[5. The apparatus of claim 1 including ligand attached to carrier particles which compete with the unknown ligand for binding sites on the antiligand material.]

[6. The apparatus of claim 1 including antiligand attached to carrier particles to cause a binding reaction with the ligand for increasing the signal representative of the binding reaction.]

[7. The apparatus of claim 1 wherein the optical detector is on the same side of the pattern as the souree of optical radiation to detect backscattered, or reflected, radiation.]

[8. The apparatus of claim 1 wherein the optical detector is on the opposite side of the pattern as the source of optical radiation to detect forward scattered, or transmitted, radiation.]

[9. The apparatus of claim 1 wherein the ligand is attached to carrier particles which are biological entities, such as cells.]

[10. The apparatus of claim 9 wherein the ligand on the carrier particle is naturally occurring.]

[11. The apparatus of claim 1 wherein the pattern is formed by deactivating microscopic sections of an initially uniform layer of an antiligand supported on a continuous surface.]

[12. The apparatus of claim 11 in which the deactivated sections consist of a plurality of stripes each stripe having a width of microscopic dimensions and separated from each other by a constant microscopic dimension.]

[13. Apparatus for producing an output signal in accordance with a binding reaction between an antibody and an antigen, including, a spatial array of antibody having a plurality of elements of microscopic dimensions to form a predetermined pattern, antigen located in solution adjacent to the spatial array of antibody to interact with the antibody in a binding reaction in the pattern, an incident source of optical radiation and with the source being substantially coherent and monochromatic and directed to the pattern for illuminating the plurality of elements of the spatial array for producing an optical interference pattern at particular scattering angles in accordance with the modulation of the optical properties of the predetermined antibody pattern due to the binding reaction, and one or more detectors located near the pattern at one or more of the particular scattering angles to intercept the radiation and produce an output signal in accordance with the binding reaction.]

[14. The apparatus of claim 12 wherein the pattern is formed by a plurality of stripes of antibody material, each stripe having a width of microscopic dimensions and separated from each other by a constant microscopic dimension.]

[15. The apparatus of claim 13 wherein the pattern of antibody material is formed by antibody material supported on a flat continuous surface.]

[16. The apparatus of claim 13 wherein the spacial array of antibody is formed by antibody material supported on a grooved surface forming an interference grating.]

[17. The apparatus of claim 13 including antigen attached to carrier particles which competes with the unknown antigen for binding sites on the antibody material.]

[18. The apparatus of claim 13 including antibody attached to carrier particles to cause a binding reaction with the antigen for increasing the signal representative of the binding reaction.]

[19. The apparatus of claim 13 wherein the optical detector is on the same side of the pattern as the source of optical radiation to detect backscattered, or reflected, radiation.]

[20. The apparatus of claim 13 wherein the optical detector is on the opposite side of the pattern as the source of optical radiation to detect forward scattered, or transmitted radiation.]

[21. The apparatus of claim 13 wherein the antigen is attached to carrier particles which are biological entities.]

[22. The apparatus of claim 21 wherein the antigen on the carrier particle is naturally occurring.]

[23. The apparatus of claim 13 wherein the pattern is formed by deactivating microscopic sections of an initially uniform layer of an antibody supported on a continuous surface.]

[24. The apparatus of claim 23 in which the deactivated sections consist of a plurality of stripes each stripe having a width of microscopic dimensions and separated from each other by a constant microscopic dimension.]

[25. A method for providing an optical detection of a binding reaction between a ligand and an antiligand, including the following steps, forming a predetermined pattern having a spatial array having a plurality of elements of microscopic dimensions of antiligand material, providing ligand material to interact with the spatial array of antiligand material to produce a binding reaction between the ligand and the antiligand in the periodic pattern, directing optical radiation including energy of at least one wavelength to the pattern for illuminating the plurality of elements of the spatial array to produce scattering of the energy from the pattern following the physical principle of constructive optical interference in accordance with the binding reaction and with a strong scattering intensity at one or more particular scattering angles, and detecting the strong scattering intensity at one or more of the particular scattering angles to produce a signal representative of the binding reaction.]

[26. The method of claim 25 wherein the predetermined pattern is formed by a plurality of stripes of antiligand material, each stripe having a width of microscopic dimensions and separated from each other by a constant microscopic dimension.]

[27. The method of claim 26 wherein the plurality of stripes of antiligand material is formed by antiligand material supported on a flat continuous surface.]

[28. The method of claim 25 wherein the the spacial pattern of antiligand material is formed by antiligand material supported on a grooved surface forming an interference grating.]

[29. The method of claim 25 including ligand attached to carrier particles which competes with the unknown ligand for binding sites on the antiligand material.]

[30. The method of claim 25 including antiligand attached to carrier particles to cause a binding reaction with the ligand for increasing the signal representative of the binding reaction.]

[31. The method of claim 25 wherein the optical detection is on the same side of the pattern as the source of optical radiation to detect backscattered, or reflected, radiation.]

[32. The method of claim 25 wherein the optical detection is on the opposite side of the pattern as the source of optical radiation to detect forward scattered, or transmitted, radiation.]

[33. The method of claim 25 wherein the ligand is attached to carrier particles which are biological entities.]

[34. The method of claim 33 wherein the ligand on the carrier particle is naturally occurring.]

[35. The method of claim 25 wherein the pattern is formed by deactivating microscopic sections of an initially uniform layer of an antiligand.]

[36. The method of claim 35 in which the deactivated sections consist of a plurality of stripes each stripe having a width of microscopic dimensions and separated from each other by a constant microscopic dimension.]

[37. A method for producing an output signal in accordance with a binding reaction between an antibody and an antigen, including the following steps, providing a spatial array of antibody having a plurality of elements of microscopic dimensions to form a predetermined pattern, locating antigen in solution adjacent to the spatial array of antibody to interact with the antibody in a binding reaction in the pattern, directing substantially coherent and monochromatic optical radiation to the pattern for illuminating the plurality of elements of the spatial array for producing scattering from the pattern at particular scattering angles due to optical interference in accordance with the binding reaction, and detecting the scattered radiation to produce an output signal in accordance with the binding reaction.]

[38. The method of claim 37 wherein the regular pattern is formed by a plurality of stripes of antibody material, each stripe having a width of microscopic dimensions and separated from each other by a constant microscopic dimension.]

[39. The method of claim 38 wherein the plurality of stripes of antibody material is formed by antibody material supported on a flat continuous surface.]

[40. The method of claim 37 wherein the spacial pattern of antibody material is formed by antibody material supported on a grooved surface forming an interference grating.]

[41. The method of claim 37 including antigen attached to carrier particles which competes with the unknown antigen for binding sites on the antigen material.]

[42. The method of claim 37 including antibody attached to carrier particles to cause a binding reaction with the antigen for increasing the signal representative of the binding reaction.]

[43. The method of claim 37 wherein the optical detection is on the same side of the pattern as the source of optical radiation to detect backscattered, or reflected, radiation.]

[44. The method of claim 37 wherein the optical detection is on the opposite side of the pattern as the source of optical radiation to detect forward scattered, or transmitted, radiation.]

[45. The method of claim 37 wherein the antigen is attached to carrier particles which are biological entities.]

[46. The method of claim 45 wherein the antigen on the carrier particle is naturally occurring.]

[47. The method of claim 37 wherein the pattern is formed by deactivating microscopic sections of an initially uniform layer of an antiligand.]

[48. The method of claim 47 in which the deactivated sections consist of a plurality of stripes each stripe having a width of microscopic dimensions and separated from each other by a constant microscopic dimension.]

*49. A flat immunoassay substrate having a uniform coating thereon, the uniform coating comprising an immunochemical optical interference pattern of microscopic dimensions of alternating areas of an active and deactivated member of a binding pair consisting of ligand and antiligand, the uniform coating having effectively uniform scattering properties and having a minimum scattering intensity at Bragg angles $\theta_s$, the pattern of alternating areas forming an optical interference grating with a detectable scattering intensity at Bragg angles $\theta_s$ if the one member of the binding pair is bound to the other member of the binding pair.*

*50. A flat immunoassay substrate of claim 49 wherein the minimum scattering intensity at Bragg angles $\theta_s$ is close to zero when ligand is not bound to the active antiligand.*

*51. A flat immunoassay substrate of claim 49 wherein the ligand is an analyte and the antiligand is a receptor which binds with the analyte.*

*52. A flat immunoassay substrate of claim 49 wherein the binding pair consists of an antigen or hapten, and an antibody which binds therewith.*

*53. A flat immunoassay substrate of claim 49 wherein the areas of active member of the binding pair are bound with the other member of the binding pair.*

*54. A flat immunoassay substrate of claim 53 wherein said other member of the binding pair is attached to a label consisting of additional scattering mass.*

*55. A flat immunoassay substrate of claim 53 wherein said other member of the binding pair is additionally*

*bound with another binding agent binding specifically therewith consisting of ligand or antiligand.*

*56. A flat immunoassay substrate of claim 55 wherein the other member of the binding pair is attached to a label consisting of additional scattering mass.*

*57. A flat immunoassay substrate of claim 56 wherein the other member of the binding pair is attached to a carrier particle.*

*58. A flat immunoassay substrate of claim 53 wherein the other member of the binding pair is located on the surface of a biological entity.*

*59. A flat immunoassay substrate of claim 57 wherein the biological entity is a cell.*

*60. A flat immunoassay substrate of claim 53 wherein the other member of the binding pair is attached to a carrier particle.*

*61. An apparatus for providing an optical detection of a binding reaction between a ligand and an antiligand, including,*

*a. a flat immunoassay substrate having a uniform coating thereon, the uniform coating comprising an immunochemical optical interference pattern of microscopic dimensions of alternating areas of an active and deactivated member of a binding pair consisting of ligand and antiligand, the uniform coating having effectively uniform scattering properties and having a minimum scattering intensity at Bragg angles $\theta_s$, the pattern of alternating areas forming an optical interference grating with a detectable scattering intensity at Bragg angles $\theta_s$ if the one member of the binding pair is bound to the other member of the binding pair.*

*b. a source of optical radiation directed toward the pattern to illuminate the alternating areas of active and deactivated member of the binding pair of produce a detectable scattering intensity in accordance with the predetermined antiligand pattern due to the binding reaction, and*

*c. one or more optical detectors to detect the scattering intensity of the scattering signal at one or more Bragg angles to produce a signal representative of the binding reaction.*

*62. An apparatus of claim 61 wherein the minimum scattering intensity at Bragg angles $\theta_s$ is close to zero when ligand is not bound to the active antiligand.*

*63. An apparatus of claim 61 wherein the ligand is an analyte and the antiligand is a receptor which binds with the analyte.*

*64. An apparatus of claim 61 wherein the binding pair consists of an antigen or hapten, and an antibody which binds therewith.*

*65. An apparatus of claim 61 wherein the areas of active member of the binding pair are bound with the other member of the binding pair.*

*66. An apparatus of claim 65 wherein said other member of the binding pair is attached to a label consisting of additional scattering mass.*

*67. An apparatus of claim 65 wherein said other member of the binding pair is additionally bound with a another binding agent binding specifically therewith consisting of ligand or antiligand.*

*68. An apparatus of claim 67 wherein the other member of the binding pair is attached to a label consisting of additional scattering mass.*

*69. An apparatus of claim 68 wherein the other member of the binding pair is attached to a carrier particle.*

*70. An apparatus of claim 65 wherein the other member of the binding pair is located on the surface of a biological entity.*

*71. An apparatus of claim 70 wherein the biological entity is a cell.*

*72. An apparatus of claim 65 wherein the other member of the binding pair is attached to a carrier particle.*

*73. An apparatus of claim 61 wherein the optical detector is on the same side of the pattern as the source of optical radiation to detect backscattered, or reflected, radiation.*

*74. An apparatus of claim 61 wherein the optical detector is on the opposite side of the pattern as the source of optical radiation to detect forward scattered, or transmitted, radiation.*

*75. A method for providing an optical detection of a binding reaction between a ligand and an antiligand, including the steps of*

*a. interacting ligand material with a flat immunoassay substrate having a uniform coating thereon, the uniform coating comprising an immunochemical optical interference pattern of microscopic dimensions of alternating areas of an active and deactivated member of a binding pair consisting of ligand and antiligand, the uniform coating having effectively uniform scattering properties and having a minimum scattering intensity at Bragg angles $\theta_s$, the pattern of alternating areas forming an optical interference grating with a detectable scattering intensity at Bragg angles $\theta_s$ if the one member of the binding pair is bound to the other member of the binding pair,*

*b. directing optical radiation including energy of at least one wavelength toward the pattern to illuminate the alternating areas of active and deactivated member of the binding pair to produce a detectable scattering intensity in accordance with the predetermined antiligand pattern due to the binding reaction, and*

*c. detecting the scattering intensity at one or more of the particular scattering angles to produce a signal representative of the binding reaction.*

*76. A method of claim 75 wherein the optical detection is on the same side of the pattern as the source of optical radiation to detect backscattered, or reflected, radiation.*

*77. A method of claim 75 wherein the optical detection is on the opposite side of the the pattern as the source of optical radiation to detect forward scattered, or transmitted, radiation.*

*78. A method of claim 75 wherein the minimum scattering intensity at Bragg angles $\theta_s$ is close to zero when ligand is not bound to the active antiligand.*

*79. A method of claim 75 wherein the ligand is an analyte and the antiligand is a receptor which binds with the analyte.*

*80. A method of claim 75 wherein the binding pair consists of an antigen or hapten, and an antibody which binds therewith.*

*81. A method of claim 75 wherein the areas of active member of the binding pair are bound with the other member of the binding pair.*

*82. A method of claim 81 wherein said other member of the binding pair is attached to a label consisting of additional scattering mass.*

*83. A method of claim 81 wherein said other member of the binding pair is additionally bound with a another binding agent consisting of ligand or antiligand binding specifically therewith.*

*84. A method of claim 83 wherein the other member of the binding pair is attached to a label consisting of additional scattering mass.*

*85. A method of claim 83 wherein the other member of the binding pair is attached to a carrier particle.*

*86. A method of claim 81 wherein the other member of the binding pair is located on the surface of a biological entity.*

*87. A method of claim 86 wherein the biological entity is a cell.*

*88. A method of claim 87 wherein the other member of the binding pair is attached to a carrier particle.*

* * * * *